(12) United States Patent
Qiu et al.

(10) Patent No.: US 10,718,714 B2
(45) Date of Patent: Jul. 21, 2020

(54) PORTABLE ULTRAVIOLET EXCITED FLUORESCENCE INTENSITY DETECTOR

(71) Applicant: HENKEL (CHINA) INVESTMENT CO., LTD., Shanghai (CN)

(72) Inventors: Jianlin Qiu, Guangdong (CN); Zhiguo Lu, Guangdong (CN); Yong Chen, Guangdong (CN)

(73) Assignee: Henkel (China) Investment Co. Ltd., Shanghai (CN)

( * ) Notice: Subject to any disclaimer, the term of this patent is extended or adjusted under 35 U.S.C. 154(b) by 0 days.

(21) Appl. No.: 16/205,570

(22) Filed: Nov. 30, 2018

(65) Prior Publication Data

US 2019/0107488 A1    Apr. 11, 2019

Related U.S. Application Data

(63) Continuation of application No. PCT/CN2017/086947, filed on Jun. 2, 2017.

(30) Foreign Application Priority Data

Jun. 2, 2016 (WO) ................ PCT/CN2016/084511

(51) Int. Cl.
*G01N 21/64* (2006.01)
*G01N 21/84* (2006.01)
*A61F 13/84* (2006.01)

(52) U.S. Cl.
CPC ........... *G01N 21/645* (2013.01); *G01N 21/84* (2013.01); *A61F 2013/8473* (2013.01); *G01N 2021/6421* (2013.01); *G01N 2021/6465* (2013.01); *G01N 2021/6471* (2013.01); *G01N 2201/0221* (2013.01); *G01N 2201/064* (2013.01)

(58) Field of Classification Search
CPC .. G01N 21/645; G01N 21/6489; G02B 21/16; A61G 2013/8473
See application file for complete search history.

(56) References Cited

U.S. PATENT DOCUMENTS

| | | | |
|---|---|---|---|
| 5,412,219 A | 5/1995 | Chappelle et al. | |
| 2002/0079454 A1* | 6/2002 | Yamada | ................. G07D 7/121 250/358.1 |
| 2003/0048445 A1 | 3/2003 | Tokhtuev et al. | |
| 2003/0057053 A1 | 3/2003 | Kano et al. | |
| 2003/0164457 A1* | 9/2003 | Kumakura | ......... G01N 21/6428 250/459.1 |
| 2005/0186565 A1 | 8/2005 | Malak | |
| 2005/0236481 A1* | 10/2005 | Gascoyne | ............ G01N 21/643 235/454 |

(Continued)

FOREIGN PATENT DOCUMENTS

| | | |
|---|---|---|
| CN | 101122567 A | 2/2008 |
| CN | 104483301 A | 4/2015 |

(Continued)

*Primary Examiner* — Yara B Green
(74) *Attorney, Agent, or Firm* — Steven C. Bauman (57) ABSTRACT

The present application discloses a portable ultraviolet excited fluorescence intensity detector for carrying out quantitative fluorescence detection for a disposable hygiene product's raw materials and a method of using the same, comprising a housing, an ultraviolet emitting light path, a first receiving light path and a second receiving light path

14 Claims, 4 Drawing Sheets

(56) References Cited

U.S. PATENT DOCUMENTS

2009/0137908 A1     5/2009   Patwardhan
2010/0184117 A1     7/2010   Cerovic et al.

FOREIGN PATENT DOCUMENTS

| CN | 104568858 | A | 4/2015 |
|---|---|---|---|
| CN | 105004701 | A | 10/2015 |
| CN | 105223177 | A | 1/2016 |
| EP | 0736767 | A1 | 10/1996 |
| JP | 2003067805 | A | 3/2003 |
| WO | 03089661 | A1 | 10/2003 |
| WO | 2010146758 | A1 | 12/2010 |

* cited by examiner

PORTABLE ULTRAVIOLET EXCITED FLUORESCENCE INTENSITY DETECTOR

FIELD OF THE INVENTION

The present application generally relates to a portable ultraviolet excited fluorescence intensity detector allowing quantitative fluorescence detection of raw materials of a disposable hygiene product.

BACKGROUND OF THE INVENTION

Disposable hygiene products such as a paper diaper, a sanitary towel or the like are generally composed of a hot-melt adhesive and non-hot-melt-adhesive-type base materials such as nonwovens, absorbent materials, polyethylene films or the like. For the sake of production and appealing appearance, the non-hot-melt-adhesive type base material sometimes may be added with fluorescent substance. Further, the hot-melt adhesive itself has fluorescent composition. However, as customers pay more attention to their personal health, it becomes more important to determine fluorescence intensity of the disposable hygiene product and, therefore, relevant regulatory requirements become stricter.

In order to detect the fluorescence intensity of the disposable hygiene product, a known method is to place an object to be tested, for example an adhesive or non-hot-melt-adhesive type base material, into a testing black box, radiate the object to be tested by ultraviolet, and then view the intensity of fluorescence excited by the ultraviolet through human eyes. In this way, whether the fluorescence intensity of the object is out of limits may be evaluated. However, different testing persons' eyes are different in term of fluorescence sensitivity. Therefore, it is very hard to carry out quantitative fluorescence detection for the object to be tested only by human eyes. It is impossible to provide an objective assessment standard for the disposable hygiene products with regard to fluorescence intensity.

Furthermore, although it is possible to carry out quantitative fluorescence detection for disposable napkins, such detection requires dissolving the napkins, and such detection takes longer time and thus is not suitable for quick fluorescence detection of the disposable hygiene products.

SUMMARY OF THE INVENTION

In order to solve the problems mentioned previously, the present application aims at proposing a portable ultraviolet excited fluorescence intensity detector by which quantitative fluorescence detection can be made to both a hot-melt adhesive and a non-hot-melt-adhesive-type base material of a disposable hygiene product. Further, such detection will take shorter time and thus is adequate for production and operating activities.

In one aspect of the present application, a portable ultraviolet excited fluorescence intensity detector for carrying out quantitative fluorescence detection for a disposable hygiene product's raw materials is proposed, wherein the detector comprises a housing, wherein a detection opening is formed in a planar sidewall of the housing, an ultraviolet emitting light path, a first receiving light path and a second receiving light path are defined within the housing such that these light paths are coplanar, wherein after the portable ultraviolet excited fluorescence intensity detector is placed on a planar substrate to be tested, the ultraviolet emitting, first receiving and second receiving light paths converge at a point in a surface of the planar substrate, wherein an ultraviolet source is arranged in the ultraviolet emitting light path and is adapted to emit ultraviolet light towards the point and excite fluorescence there, a first sensor and a second sensor are arranged in the first receiving light path and the second receiving light path respectively such that the sensors can be selectively operated, wherein the first sensor is designed to convert light, whose wavelength is between 420 and 480 nm, into electric signals proportional to the light intensity, the second sensor is designed to convert light, whose wavelength is between 480 and 760 nm, into electric signals proportional to the light intensity, and wherein a first filter device and a second filter device are allocated to the first and second sensors respectively such that the excited fluorescence can be received by the first and second sensors through the first and second filter devices respectively.

Optionally, the first receiving light path and the second receiving light path are mirror-symmetrical relative to a plane passing through the converging point and perpendicular to the planar sidewall.

Optionally, the ultraviolet emitting light path and the first receiving light path are at the same side relative to the plane.

Optionally, the ultraviolet emitting light path is sloped at a first angle relative to the planar sidewall, the first receiving and second receiving light paths are sloped at a second angle relative to the planar sidewall, and the first angle is less than the second angle.

Optionally, the first angle is between 10 and 45 degrees, the second angle is between 15 and 60 degrees and, preferably, is 60 degrees.

Optionally, the first filter device comprises an ultraviolet filter and a first fluorescence filter enabling light, whose wavelength is greater than 480 nm, to be filtered out, and the excited fluorescence passes through the ultraviolet filter and the first fluorescence filter in this order.

Optionally, the second filter device comprises an ultraviolet filter and a second fluorescence filter enabling light, whose wavelength is less than 480 nm, to be filtered out, and the excited fluorescence passes though the ultraviolet filter and the second fluorescence filter in this order.

Optionally, the ultraviolet light emitting from the ultraviolet source has a wavelength in the range between 320 nm and 400 nm, preferably of 365 nm.

Optionally, the detector comprises a liquid crystal display on which the electric signals can be displayed in digital format.

Optionally, the detector further comprises a shade structure for preventing ambient light from entering the detection opening when the housing of the portable ultraviolet excited fluorescence intensity detector contacts the planar substrate.

Optionally, the detector further comprises a storage device in which the electric signals can be stored in readable format.

Optionally, the detector further comprises a retainer within the housing, formed in the retainer are an ultraviolet source installing hole for defining the ultraviolet emitting light path, a hot-melt-adhesive detecting passage for defining the first receiving light path, and a non-melt-adhesive-type base material detecting passage for defining the second receiving light path, the ultraviolet source is secured within the ultraviolet source installing hole, the first sensor and the first filter device are secured within the hot-melt-adhesive detecting passage, and the second sensor and the second filter device are secured within the non-melt-adhesive-type base material detecting passage.

In another aspect of the present application, a method for carrying out quantitative fluorescence detection for a disposable hygiene product's raw materials by said portable ultraviolet excited fluorescence intensity detector as mentioned previously is proposed, wherein the raw material comprises a hot-melt adhesive and a non-hot-melt-adhesive-type base material, the method comprises: preparing the hot-melt adhesive or non-hot-melt-adhesive-type base material as a planar substrate to be tested; placing the portable ultraviolet excited fluorescence intensity detector onto the planar substrate such that a detection opening of the detector faces the planar substrate; selectively activating a first or second sensor of the detector depending on the substance used for preparing the substrate; and powering on an ultraviolet source of the detector such that the activated sensor can convert excited fluorescence into electric signals proportional to its light intensity.

Optionally, the method further comprises: displaying the electric signals in digital format in real time on a liquid crystal display of the portable ultraviolet excited fluorescence intensity detector.

Other individual features or features which are combined with other features so as to be considered as belonging to the characteristic of the present invention will be described in the attached claims.

The configuration of the present invention and other objectives and beneficial effects thereof will be well understood by description of preferred embodiment in accompany of the drawings.

BRIEF DESCRIPTION OF THE DRAWINGS

As a part of the description and in order to provide further explanation of the present invent, the drawings illustrate preferred embodiments of the present invention, and together with the description are used to explain the principle of the present invention. In the drawings.

DETAILED DESCRIPTION OF PREFERRED EMBODIMENTS

In the drawings of the present application, features having the same configuration or function are represented by the same reference numerals. Although those drawings are prepared in different scales, this cannot be deemed giving any limitation to the present application.

Due to personal visual sensitivity, the same operator has different sensitivities for lights with different wavelengths. The inventor found that ultraviolet excited fluorescence of a hot-melt-adhesive-type material generally has a wavelength range of blue and purple light band, and ultraviolet excited fluorescence of a non-hot-melt-adhesive-type material generally has a wavelength of green and red light band. However, sensitivities of human eyes to red, green and blue lights decrease in this order. Therefore, for an operator, when his/her eyes are adequate for the ultraviolet excited fluorescence of the non-hot-melt-adhesive-type material, it is most likely that the eyes are inadequate for the ultraviolet excited fluorescence of the hot-melt-adhesive-type material. Therefore, it is hard to make objective fluorescence evaluation only with the aid of viewing by human eyes.

Figure 1:
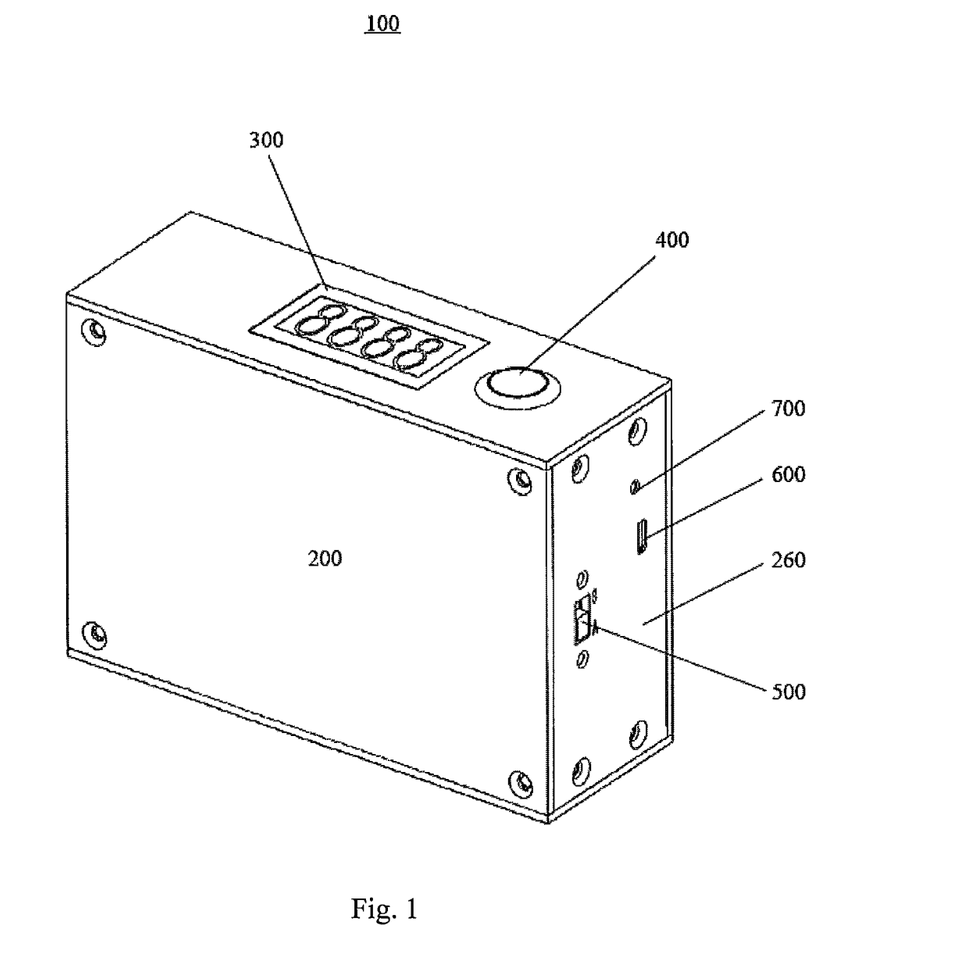
FIG. 1 is a perspective view schematically illustrating a portable ultraviolet excited fluorescence intensity detector according to an embodiment of the present application.

To this end, the present application proposes a portable ultraviolet excited fluorescence intensity detector 100. FIG. 1 schematically illustrates an embodiment of the detector. The portable ultraviolet excited fluorescence intensity detector 100 can be readily handheld by the operator and can be placed on a planar test sample. Using a switch, the portable ultraviolet excited fluorescence intensity detector can be selectively used to carry out quantitative fluorescence detection for the hot-melt-adhesive-type material or the non-hot-melt-adhesive-type material. Therefore, the problem that objective fluorescence evaluation cannot be carried out because of human eyes' viewing difference can be solved.

According to the present application, as shown in FIG. 1, the portable ultraviolet excited fluorescence intensity detector 100 generally comprises a housing 200, a liquid crystal display 300, an ultraviolet radiating button 400, a test sample selecting switch 500, a USB interface 600 and a zeroing button 700, wherein the latters are in the housing 200. For example, the housing 200 can be made of plastics or lightweight metals. The liquid crystal display 300 is used to display fluorescence inspection results thereon.

Figure 2:
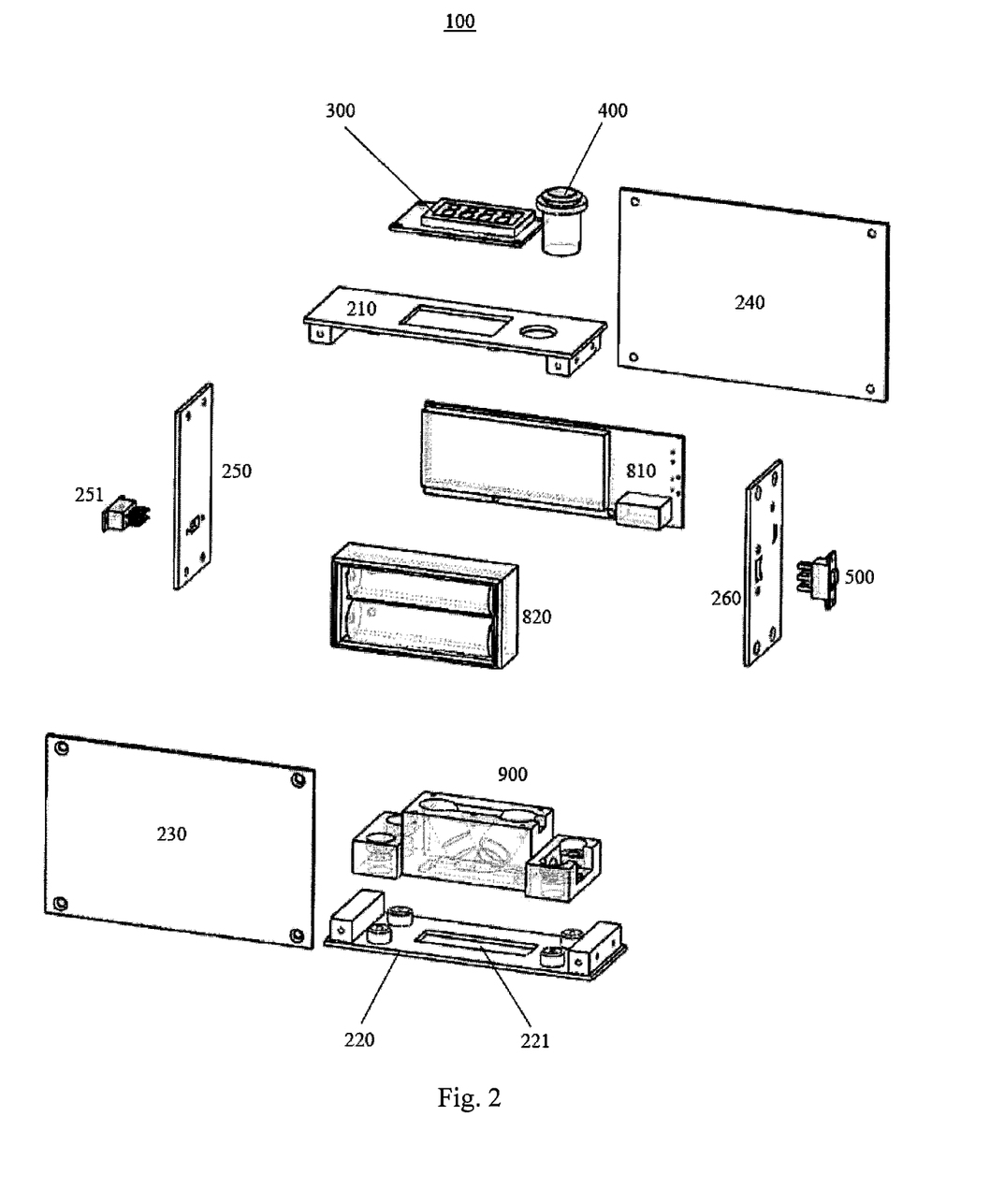
FIG. 2 is an exploded and perspective view schematically illustrating the portable ultraviolet excited fluorescence intensity detector of FIG. 1.

Further as shown in FIG. 2, the housing 200 generally comprises a top panel 210, a bottom panel 220 (hidden in FIG. 1), a front panel 230, a rear panel 240, a left panel 250 (hidden in FIG. 1) and a right panel 260. It should be understood that in the context of the present application, for the portable ultraviolet excited fluorescence intensity detector, terms "top" and 'bottom' are defined relative to the horizontal plane, terms of "front", "rear" "left" and "right" are defined by referring to those viewed in FIG. 1. The top panel 210, the bottom panel 220, the front panel 230, the rear panel 240, the left panel 250 and the right panel 260 can be secured together by screws to form the housing 200.

The liquid crystal display 300 and the ultraviolet radiating button 400 are arranged in the top panel 210. The test sample selecting button 500, the USB interface 600 and the zeroing button 700 are arranged in the right panel 260. Furthermore, a power switch 251 can be arranged in the left panel 250. A detection opening 221 is formed in the bottom panel 220. In a preferred embodiment, the detection opening 221 is substantially long-strip shaped.

A circuit board 810, a batter assembly 820 and a retainer 900 are received within the housing 200. The retainer 900 can be made of the same material as the housing 200. The retainer 900 is used to install an electric component for radiating ultraviolet and electric components for receiving ultraviolet excited fluorescence (explained in the following). The battery assembly 820 is used to supply electric power to all electric components of the detector. The circuit board 810 is provided with integrated circuits for controlling relevant electric components, integrated circuits for data acquisition and display, and a memory for storing data or the like.

The liquid crystal display 300, the ultraviolet radiating button 400, the test sample selecting button 500, the USB interface 600, the zeroing button 700, and the power switch 251 can be electrically connected to the circuit board 810 by conducting wires or other suitable means.

For example, in case that the battery assembly 820 comprises a rechargeable battery, the USB interface 600 can be configured such that the battery can be recharged by an external power supply via the USB interface. Alternatively or additionally, the USB interface 600 can be connected to a computer via a USB cable such that stored data in the detector can be copied into the computer. Optionally, the battery assembly 820 can be configured in a removable manner such that a 18650-type high performance battery (non-rechargeable) can be conveniently installed or replaced.

The retainer 900 is secured by screws at a side of the bottom panel 220 facing the interior of the housing 200. A person skilled in the art should understand that any suitable means can be applied to secure the circuit board 810 and the battery assembly 820 within the housing 200.

Figure 3:
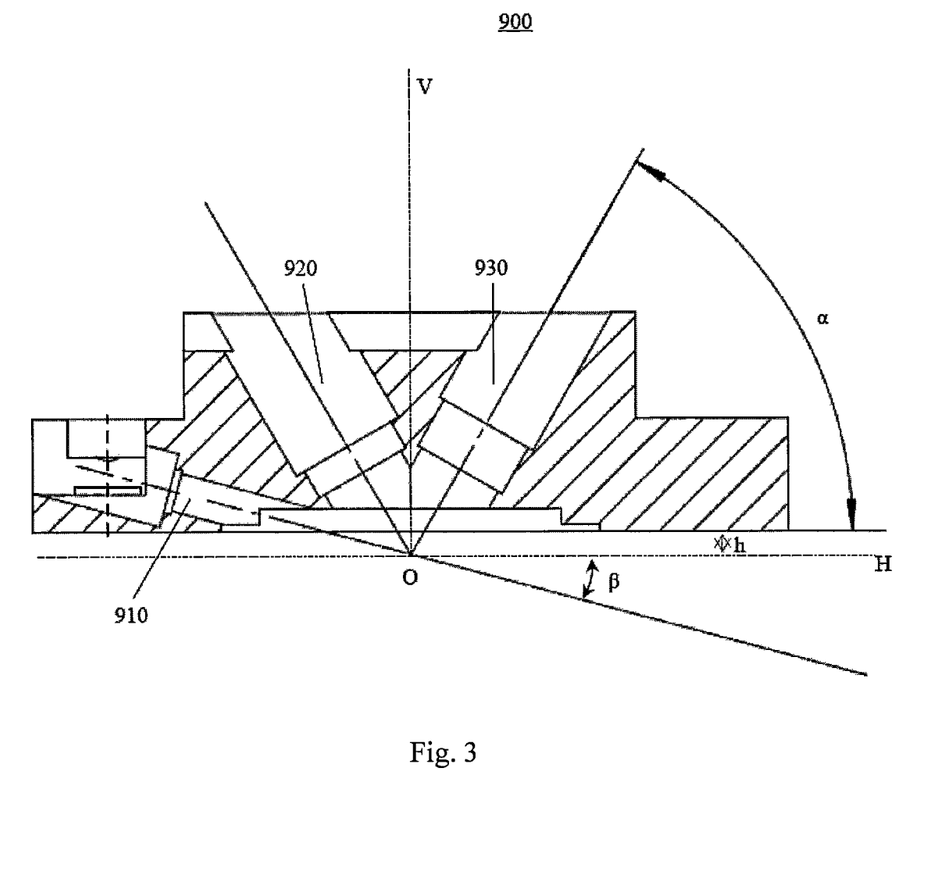
FIG. 3 is a cross-sectional view schematically illustrating a part of a retainer according to an embodiment of the present application and used for the portable ultraviolet excited fluorescence intensity detector.

As shown in FIG. 3, the retainer 900 comprises a body in which an ultraviolet source installing hole 910, a hot-melt-adhesive detecting passage 920 and a non-melt-adhesive-type base material detecting passage 930 are formed. An aperture 940 is formed in a bottom of the body of the retainer 900. The ultraviolet source installing hole 910, the hot-melt-adhesive detecting passage 920 and the non-melt-adhesive-type base material detecting passage 930 are in communication with the aperture 940. Further, the aperture 940 is sized such that it is matable with the detection opening 221 in the bottom panel 220. After the retainer 900 is secured on the bottom panel 220, the aperture 940 is directly opposite to the detecting opening 221.

Furthermore, a central axis of the ultraviolet source installing hole 910, a central axis of the hot-melt-adhesive detecting passage 920, and a central axis of the non-melt-adhesive-type base material detecting passage 930 are coplanar. Those central axes converge at a point O in an imaginary plane H which is spaced from a bottom surface of the body of the retainer 900 by a distance h. The distance h is equal to a thickness of the bottom panel 220.

Figure 4:
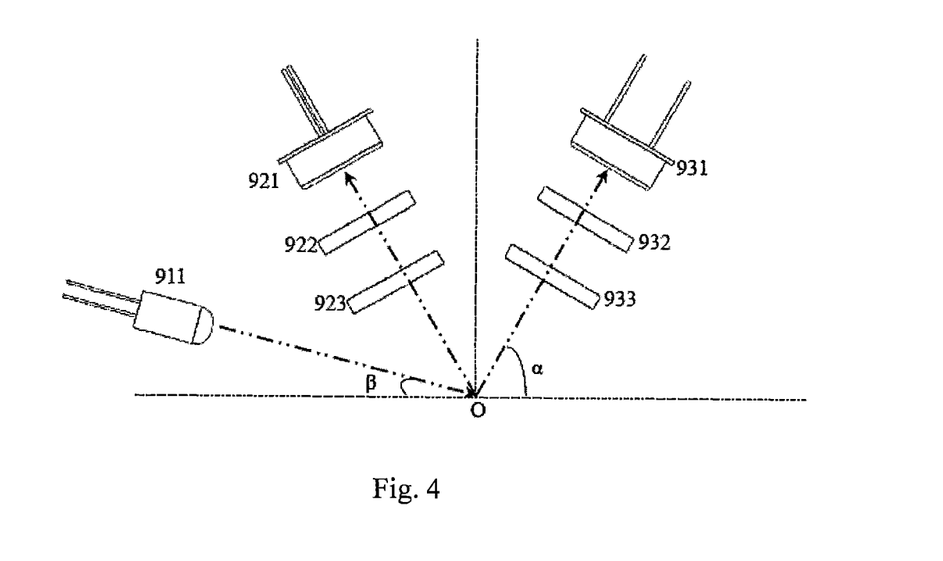
FIG. 4 schematically illustrates components installed in the retainer of FIG. 3.

As shown in FIG. 4, a fluorescence source 911, for example a fluorescence lamp or LED, is securely installed in the ultraviolet source installing hole 910 such that ultraviolet light emitting from the fluorescence source 911 can propagate towards the aperture 940 along the central axis of the ultraviolet source installing hole 910. The ultraviolet source 911 is designed to emit ultraviolet light whose power is constant and whose wavelength is in the range between 320 nm and 400 nm. Preferably, the wavelength of the emitted ultraviolet light is 365 nm.

A first sensor 921, a first fluorescence filter 922 and an ultraviolet filter 923 are securely installed in this order in the hot-melt-adhesive detecting passage 920 such that the first sensor, the first fluorescence filter and the ultraviolet filter are located from distal to proximal towards the aperture 940. The first sensor 921 is designed to convert blue and purple light, whose wavelength is in the range between 420 nm and 480 nm, into electric signals proportional to its light intensity. The first fluorescence filter 922 is designed to filter out light whose wavelength is greater than the wavelength of the blue and purple light. That is to say, the first fluorescence filter is adapted to filter out light whose wavelength is greater than 480 nm. In this way, in case that a surface of an object to be tested coincides with the imaginary plane H, when the ultraviolet light emitting from the ultraviolet source 911 propagates at the point O, fluorescence will be excited at the point O. Then, the excited fluorescence will first pass through the ultraviolet filter 923 along the passage 920, at which ultraviolet filter 923 the ultraviolet light emitting from the ultraviolet source 911 will be filtered out. Afterwards, the fluorescence will pass through the first fluorescence filter 922, at which the light whose wavelength is greater than the wavelength of the blue and purple light will be filtered out. Finally, only the blue and purple light will substantially arrive at the first sensor 921 at which the light will be converted into proportional electric signals.

A second sensor 931, a second fluorescence filter 932 and an ultraviolet filter 933 are securely installed in this order in the non-melt-adhesive-type base material detecting passage 930 such that the second sensor, the second fluorescence filter and the ultraviolet filter are located from distal to proximal towards the aperture 940. For example, the second sensor 931 can be a visible light (full spectrum) sensor. Preferably, the second sensor is designed to convert light, whose wavelength is in the range between 480 nm and 760 nm (mainly red and blue light), into electric signals proportional to its light intensity. However, this second sensor is not sensitive to the blue and purple light. The second fluorescence filter 932 is designed to filter out light whose wavelength is less than the wavelength of green light (less than 480 nm). In this way, in case that the surface of the object to be tested coincides with the imaginary plane H, when the ultraviolet light emitting from the ultraviolet source 911 propagates at the point O, the fluorescence light is excited at the point O. Then, the excited fluorescence will first pass through the ultraviolet filter 933 along the passage 930, at which ultraviolet filter 933 the ultraviolet light emitting from the ultraviolet source 911 will be filtered out. Afterwards, the fluorescence will pass through the second fluorescence filter 932, at which light, whose wavelength is less than the wavelength of the green light, is filtered out. Finally, the filtered fluorescence will arrive at the second sensor 931 and will be converted into proportional electric signals.

As explained previously, the ultraviolet source installing hole 910 can be deemed to define an ultraviolet emitting light path (which is parallel to the central axis of the ultraviolet source installing hole 910), the hot-melt-adhesive detecting passage 920 can be deemed to define a first receiving light path (which is parallel to the central axis of the hot-melt-adhesive detecting passage 920), and the non-melt-adhesive-type base material detecting passage 930 can be deemed to define a second receiving light path (which is parallel to the central axis of the non-melt-adhesive-type base material detecting passage 930). Preferably, the three light paths are coplanar. Here, coplanar means that the three light paths' central axes are in the same plane. Preferably, the first receiving light path and the second receiving light path are mirror-symmetrical relative to a vertical plane V passing through the point O and perpendicular to the plane H. That is to say, the first receiving light path and the second receiving light path are located at both sides of the vertical plane V respectively, and are at the same angle α relative to the plane H. For instance, the angle α is in the range between 15 and 60 degrees. The skilled person in the art should understand that, the first and second receiving light paths can be arranged such that they are not mirror-symmetrical relative to the vertical plane V. In this case, the first and second receiving light paths are at different angles relative to the plane H.

The ultraviolet emitting light path and the first receiving light path are at the same side relative to the vertical plane V, and the ultraviolet emitting light path is at an angle β relative to the plane H (i.e. relative to a planar bottom side of the housing), wherein β<α. For example, the angle β is in the range between 10 and 45 degrees. According to experiments carried out by the inventor, when the angle α is 60 degrees and the angle β is in the range between 10 and 45 degrees, optimal testing results can be obtained.

The skilled person in the art should understand that the ultraviolet emitting light path can be configured such that this light path and the second receiving light path are at the same side relative to the vertical plane V.

The test sample selecting switch 500 is provided such that the first sensor 921 or the second sensor 931 can be selectively operated. The ultraviolet radiating button 400 is provided to activate the ultraviolet source 911 to emit the ultraviolet light. The zeroing button 700 is provided such that after it is depressed, a zeroing circuit in the circuit board 810 is operated to reset relevant electric components and thus to eliminate a so-called zero drift effect caused by temperature difference.

When the portable ultraviolet excited fluorescence intensity detector 100 according to the present application is used to carry out quantitative fluorescence detection, the hot-melt adhesive or non-hot-melt-adhesive-type base material is first prepared as a substrate to be tested. For the hot-melt adhesive, it is melt in a planar mold and solidified to have at least a planar upper surface. For the non-hot-melt-adhesive-type base material, for example non-woven fabric, it is laid on a planar surface to form the substrate to be tested.

Then, the power switch 251 is activated on such that the portable ultraviolet excited fluorescence intensity detector 100 can be powered on and self-inspected. Now, the liquid crystal display 300 can show relevant self-inspection information. After the self-inspection, the portable ultraviolet excited fluorescence intensity detector 100 is set idle for a period, for example 30 minutes, such that the sensors can enter a stable state.

Subsequently, the portable ultraviolet excited fluorescence intensity detector 100 is placed on the substrate to be tested in such a way that the detection opening 221 of the portable ultraviolet excited fluorescence intensity detector 100 faces the substrate to be tested and the plane H can coincide with the upper surface of the substrate to be tested. Now, no ambient light can enter between the detector 100 and the substrate to be tested. Optionally, now, the zeroing button 700 can be depressed so as to reset the sensors and relevant data can be shown on the liquid crystal display 300 for the operator's reference. For example, the electric signals detected by the sensors can be successively shown in digital format on the liquid crystal display 300.

Depending on the targeted substrate material, the test sample selecting switch 500 can be operated to enable a corresponding sensor to be activated. Optionally, after one sensor is selected, the detector 100 can be used to carry out the self-inspection in a manner mentioned previously.

When numeral reading of the liquid crystal display 300 becomes zero, that is to say when the sensors are completely zeroed, the ultraviolet radiating button 400 is depressed such that the ultraviolet light will excite the fluorescence, which will be detected by the selected sensor and relevant reading will be shown on the liquid crystal display 300 and be kept for a period of for example 6 seconds.

Optionally, after each self-inspection, the quantity of electricity of the battery assemble 820 is inspected and shown on the liquid crystal display 300. If the quantity of electricity is less than a predefined value, a warning will be shown on the liquid crystal display 300 to urge the operator to recharge or replace the battery.

In order to ensure that no ambient light can enter between the detector 100 and the substrate after the detector is placed on the substrate, a shade structure can be provided around the housing of the detector 100. For example, a soft rubber strip or any other suitable shade means can be provided circumferentially on an outer wall at the housing bottom such that any possible gap between the detector 100 and the substrate can be sealed off.

Although the ultraviolet source installing hole 910, the hot-melt-adhesive detecting passage 920 and the non-melt-adhesive-type base material detecting passage 930 are formed in the body of the retainer 900, they can be allocated with separate retainers respectively as long as the ultraviolet emitting, first receiving and second receiving light paths can meet requirements mentioned previously.

Using the portable ultraviolet excited fluorescence intensity detector of the present application, the quantitative fluorescence detection of the hot-melt adhesive or the non-hot-melt-adhesive-type base material of the disposable hygiene product can be carried out without needing human eyes. Such quantitative fluorescence detection can provide basis for production quality control of the disposable hygiene product's raw material in term of fluorescent residuals.

Although several embodiments according to the present application have already been explained, they are given as examples only and cannot be considered to make any limitation to the scope of the present application. The embodiments can be carried out in other suitable manners, and their alternations, changes or modifications can be made without departing from the spirit of the present application. Those embodiments and their modifications should be deemed as being included in the scope and content of the present application, and included in the application recorded by appended claims and theirs equivalents.

The invention claimed is:

1. A portable ultraviolet excited fluorescence intensity detector for carrying out quantitative fluorescence detection for a disposable hygiene product's raw materials, comprising a housing, wherein a detection opening is formed in a planar sidewall of the housing in which an ultraviolet emitting light path, a first receiving light path and a second receiving light path are defined such that these light paths are coplanar, wherein after the portable ultraviolet excited fluorescence intensity detector is placed on a planar substrate to be tested, the ultraviolet emitting, first receiving and second receiving light paths converge at a point in a surface of the planar substrate, wherein an ultraviolet source is arranged in the ultraviolet emitting light path and is adapted to emit ultraviolet light towards the point and excite fluorescence there, a first sensor and a second sensor are arranged in the first receiving light path and the second receiving light path respectively such that the sensors can be selectively operated, wherein the first sensor is designed to convert light, whose wavelength is between 420 and 480 nm, into electric signals proportional to the light intensity, the second sensor is designed to convert light, whose wavelength is between 480 and 760 nm, into electric signals proportional to the light intensity, and wherein a first filter device and a second filter device are allocated to the first and second sensors respectively such that the excited fluorescence can be received by the first and second sensors through the first and second filter devices respectively.

2. The portable ultraviolet excited fluorescence intensity detector according to claim 1, wherein the first receiving light path and the second receiving light path are mirror-symmetrical relative to a plane passing through the converging point and perpendicular to the planar sidewall.

3. The portable ultraviolet excited fluorescence intensity detector according to claim 1, wherein the ultraviolet emitting light path and the first receiving light path are at the same side relative to the plane.

4. The portable ultraviolet excited fluorescence intensity detector according to claim 1, wherein the ultraviolet emitting light path is sloped at a first angle relative to the planar sidewall, the first receiving and second receiving light paths are sloped at a second angle relative to the planar sidewall, and the first angle is less than the second angle.

5. The portable ultraviolet excited fluorescence intensity detector according to claim 4, wherein the first angle is between 10 and 45 degrees, the second angle is between 15 and 60 degrees.

6. The portable ultraviolet excited fluorescence intensity detector according to claim 1, wherein the first filter device comprises an ultraviolet filter and a first fluorescence filter enabling light, whose wavelength is greater than 480 nm, to be filtered out, and the excited fluorescence passes through the ultraviolet filter and the first fluorescence filter in this order.

7. The portable ultraviolet excited fluorescence intensity detector according to claim 6, wherein the second filter device comprises an ultraviolet filter and a second fluorescence filter enabling light, whose wavelength is less than 480 nm, to be filtered out, and the excited fluorescence passes though the ultraviolet filter and the second fluorescence filter in this order.

8. The portable ultraviolet excited fluorescence intensity detector according to claim 1, wherein the ultraviolet light emitting from the ultraviolet source has a wavelength in the range between 320 nm and 400 nm.

9. The portable ultraviolet excited fluorescence intensity detector according to claim 1, wherein it comprises a liquid crystal display on which the electric signals can be displayed in digital format.

10. The portable ultraviolet excited fluorescence intensity detector according to claim 1, wherein it further comprises a shade structure for preventing ambient light from entering the detection opening when the housing of the portable ultraviolet excited fluorescence intensity detector contacts the planar substrate.

11. The portable ultraviolet excited fluorescence intensity detector according to claim 1, wherein it further comprises a storage device in which the electric signals can be stored in readable format.

12. The portable ultraviolet excited fluorescence intensity detector according to claim 1, wherein it further comprises a retainer within the housing, formed in the retainer are an ultraviolet source installing hole for defining the ultraviolet emitting light path, a hot-melt-adhesive detecting passage for defining the first receiving light path, and a non-melt-adhesive-type base material detecting passage for defining the second receiving light path, the ultraviolet source is secured within the ultraviolet source installing hole, the first sensor and the first filter device are secured within the hot-melt-adhesive detecting passage, and the second sensor and the second filter device are secured within the non-melt-adhesive-type base material detecting passage.

13. A method for carrying out quantitative fluorescence detection for a disposable hygiene product's raw materials by a portable ultraviolet excited fluorescence intensity detector according to claim 1, the raw material comprising a hot-melt adhesive and a non-hot-melt-adhesive-type base material, the method comprising:
preparing the hot-melt adhesive or non-hot-melt-adhesive-type base material as a planar substrate to be tested;
placing the portable ultraviolet excited fluorescence intensity detector onto the planar substrate such that a detection opening of the detector faces the planar substrate;
selectively activating a first or second sensor of the detector depending on the substance used for preparing the substrate; and
powering on an ultraviolet source of the detector such that the activated sensor can convert excited fluorescence into electric signals proportional to its light intensity.

14. The method according to claim 13, wherein the method further comprises: displaying the electric signals in digital format in real time on a liquid crystal display of the portable ultraviolet excited fluorescence intensity detector.

* * * * *

UNITED STATES PATENT AND TRADEMARK OFFICE
CERTIFICATE OF CORRECTION

PATENT NO. : 10,718,714 B2
APPLICATION NO. : 16/205570
DATED : July 21, 2020
INVENTOR(S) : Jianlin Qiu, Zhiguo Lu and Yong Chen

Page 1 of 1

It is certified that error appears in the above-identified patent and that said Letters Patent is hereby corrected as shown below:

In the Specification

Column 3, Line 20, change "features or features" to -- feature or features --.

Signed and Sealed this
Twenty-seventh Day of October, 2020

Andrei Iancu
*Director of the United States Patent and Trademark Office*